United States Patent [19]
Freeman

[11] Patent Number: 5,507,778
[45] Date of Patent: Apr. 16, 1996

[54] SEMIAUTOMATIC DEFIBRILLATOR WITH SYNCHRONIZED SHOCK DELIVERY

[75] Inventor: Gary A. Freeman, Newton Centre, Mass.

[73] Assignee: ZMD Corporation, Wilmington, Del.

[21] Appl. No.: 200,778

[22] Filed: Feb. 22, 1994

[51] Int. Cl.$^6$ .................................................. A61N 1/39
[52] U.S. Cl. .................................................................. 607/5
[58] Field of Search .............................................. 607/4.5

[56] References Cited

U.S. PATENT DOCUMENTS

| | | | |
|---|---|---|---|
| 3,614,955 | 10/1971 | Mirowski et al. | 128/419 D |
| 3,716,059 | 2/1973 | Welborn et al. | 128/419 D |
| 3,757,791 | 9/1973 | Berkovits | 128/419 |
| 4,088,138 | 5/1978 | Diack et al. | 128/419 |
| 4,184,493 | 1/1980 | Langer et al. | 128/419 |
| 4,202,340 | 5/1980 | Langer et al. | 128/419 |
| 4,223,678 | 9/1980 | Langer et al. | 128/419 |
| 4,296,755 | 10/1981 | Judell | 128/705 |
| 4,360,030 | 11/1982 | Citron et al. | 128/702 |
| 4,453,551 | 6/1984 | Anderson et al. | 128/704 |
| 4,475,551 | 10/1984 | Langer et al. | 128/419 |
| 4,523,595 | 6/1985 | Zibell | 128/419 |
| 4,574,810 | 3/1986 | Lerman | 128/419 |
| 4,583,553 | 4/1986 | Shah et al. | 128/704 |
| 4,619,265 | 10/1986 | Morgan et al. | 128/419 |
| 4,635,639 | 1/1987 | Hakala et al. | 128/419 |
| 4,796,620 | 1/1989 | Imran | 128/706 |
| 4,919,144 | 4/1990 | Vandehey | 128/705 |
| 4,960,123 | 10/1990 | Maker | 128/419 |
| 5,342,403 | 8/1994 | Powers et al. | 607/5 |

FOREIGN PATENT DOCUMENTS 2083363A 3/1982 United Kingdom.

OTHER PUBLICATIONS

Stratbucker et al., "Automatic Cardioversion Using Electronic Arrhythmia Logic".
Thurer et al., "Automatic Implantable Cardioverter-Defibrillator: Techniques of Implantation and Results", The annals of Toracic Surgery, vol. 42, No. 2, pp. 143–147, Aug. 1986.
Mower et al., "Automatic Implantable Cardioverter-Defibrillator Structural Characteristics", PACE, vol. 7, pp. 1332–1337, Nov.–Dec. 1984, Part II.
Mirowski et al., "The Automatic Implantable Defibrillator", PACE, vol. 5, pp. 384–401, May–Jun. 1982.
Arzbaecher et al., "Automatic Tachycardia Recognition", PACE, vol. 7, pp. 541–547, May–Jun. 1984, Part II.
Mirowski et al., "A Chronically Implanted System for Automatic Defibrillation in Active Conscious Dogs" Circulation. vol. 58, No. 1, pp. 90–94, Jul. 1978.
Jenkins et al., "Computer Diagnosis of Supraventricular and Ventricular Arrhythmias", Circulation, vol. 60, No. 5, pp. 977–985, Nov. 1979.
Langer et al., "Considerations in the development of the automatic implantable defibrillator", Medical Instrumentation, vol. 10, No. 3, May–Jun. 1976.
Hsia et al, "Genesis of Sigmoidal Dose–Response Curve During Defibrillation by Random Shock: A Theoretical Model Based on Experimental . . . ", PACE, vol. 13, pp. 1326–1342 Oct. 1990.

(List continued on next page.)

*Primary Examiner*—William E. Kamm
*Attorney, Agent, or Firm*—Fish & Richardson

[57] ABSTRACT

A semiautomatic defibrillator with the capability of delivering a synchronized shock. An advisory algorithm automatically determines whether a synchronized shock should be delivered (e.g., because a shockable tachycardia is detected) and what ECG event should trigger delivery of the shock. And following initiation of a shock by the operator, the defibrillator automatically waits until the required ECG event is detected to deliver the shock. This happens automatically, without the operator being asked to decide between a synchronized and unsynchronized shock, or having to do anything differently to deliver a synchronized shock (e.g., without having to hold a button depressed as necessary to deliver a synchronized shock in manual defibrillators). The unit delivers a shock at the end of a predetermined period if the required ECG event has not been detected, so that a shock always results when the operator initiates one.

11 Claims, 4 Drawing Sheets

OTHER PUBLICATIONS

Winkle, "The Implantable Defibrillator in Ventricular Arrhythmias", Hospital Practice, pp. 149–156, 161–165, Mar. 1983.

Cannom et al., "Implantation of the Automatic Implantable Cardioverter Defibrillator (ACID): Practical Aspects", PACE, vol. 9, pp. 793–809, Nov.–Dec. 1986, Part I.

Mirowski et al., "Standby Automatic Defibrillator", Arch Intern Med, vol. 126, pp. 158–161, Jul. 1970.

Jenkins et al., "Tachycardia Detection in Implantable Antitachycardia Devices", PACE, vol. 7, pp. 1273–1277, Nov.–Dec. 1984, Part II.

SEMIAUTOMATIC DEFIBRILLATOR WITH SYNCHRONIZED SHOCK DELIVERY

BACKGROUND OF THE INVENTION

This invention relates to semiautomatic defibrillators, in which an advisory algorithm advises an operator as to whether a shock should be delivered, and it is left to the operator to initiate delivery of the shock.

Semiautomatic defibrillators are well known. They have been in use in one form or another for nearly twenty years. An advisory algorithm analyzes a patient's electrocardiogram (ECG), and gives the operator an advisory indication of whether a shock should be delivered. Typically, the advisory algorithm analyzes the ECG for both ventricular fibrillation and shockable high rate tachycardia. If either is found, the unit will advise the operator that a shock should be delivered. The operator then simply presses a button, and the unit immediately delivers the shock. Because these units are typically used by emergency medical technicians (EMTs) with relatively little, if any, training in cardiology no indication is provided to the operator of whether the shock advisory is based on finding ventricular fibrillation or shockable tachycardia. The operator is simply advised to deliver a shock.

In manual defibrillators, the type of units used by physicians and nurses, and by highly-skilled EMTs, there is no automated analysis of the ECG by an advisory algorithm, and instead the operator makes his or her own decision whether to apply a shock based on a display of the ECG. In addition, it is typical to allow the operator to select between delivering an immediate shock, in which energy is delivered as soon as the firing buttons are depressed, or a synchronized shock, in which energy is not delivered until an R-wave has been detected. Synchronized shocks are typically used when the operator recognizes a shockable tachycardia. By synchronizing the shock, the user avoids delivery of the shock in the interval following contraction, in which the heart muscle is repolarizing and is vulnerable to being thrown into fibrillation.

Recent cardiology research has suggested that synchronized shocks may also be of benefit in treating ventricular fibrillation. Hsia et al., "Genesis of Sigmoidal Dose-Response Curve During Defibrillation by Random Shock: A Theoretical Model Based on Experimental Evidence for a Vulnerable Window During Ventricular Fibrillation," PACE, Vol. 13, pp. 1326–42 (Oct. 1990). In addition, there is other research to indicate that accurate synchronization of the shock to ventricular tachycardia improves efficacy (e.g., Li, HG, "The effects of a different shock timing during ventricular activation on the efficacy and safety of internal cardioversion for ventricular tachycardia," cited at pp. 337–8, *Defibrillation of the Heart*). This research suggests that there is a greater likelihood of successful defibrillation if the shock is delivered at a time when the absolute magnitude of the VF waveform is high or at specific points during ventricular activation with ventricular tachycardias.

Synchronized shocks are delivered in manual defibrillators by having the operator hold down the shock buttons until an R-wave is detected by the unit's circuitry. This can, in some instances, mean that the operator must know to keep the buttons depressed for as long as four seconds. And, because no shock is delivered if an R-wave is not detected, the operator must be trained to appreciate that, under such circumstances, a properly functioning defibrillator may not deliver a shock.

Automatic defibrillators represent the third general category of such devices. Such automatic units are typically the implanted type, which function without intervention by the patient or operator. In such units, the stimulus delivered is entirely determined by an algorithm, which on detecting a shockable tachycardia will ordinarily first attempt to use overdrive pacing to treat the condition, and only upon that therapy failing will move to a synchronized shock.

SUMMARY OF THE INVENTION

In general the invention features a semiautomatic defibrillator with the capability of delivering a synchronized shock. The advisory algorithm automatically determines whether a synchronized shock should be delivered (e.g., because a shockable tachycardia is detected) and what ECG event should trigger delivery of the shock. And following initiation of a shock by the operator, the defibrillator automatically waits until the required ECG event is detected to deliver the shock.

Preferably, all of this happens automatically, without the operator being asked to decide between a synchronized and unsynchronized shock, or having to do anything differently to deliver a synchronized shock (e.g., without having to hold a button depressed as necessary to deliver a synchronized shock in manual defibrillators). Also, preferably, the unit will deliver a shock at the end of a predetermined period if the required ECG event has not been detected, so that a shock always results when the operator initiates one.

The invention provides a practical and effective means of delivering a synchronized shock from a semiautomatic defibrillator, thereby avoiding delivery of a shock during the vulnerable period in tachycardia. The operator retains control of whether or not a shock is delivered, but is not expected (as with a manual defibrillator) to choose between synchronized and unsynchronized shock delivery. The operator is simply advised that a shock should be delivered, and instructed to initiate a shock by depressing a button. No indication of the need for a synchronized shock is provided, and the operator does not have to hold a button depressed, or take any other action different from what would be required for an ordinary, unsynchronized shock. Finally, having the unit deliver a shock at the end of a predetermined period, even if the required ECG event has not been detected, assures that a shock is delivered even in the unlikely event of a misdiagnosis by the advisory algorithm (e.g., a diagnosis of shockable tachycardia instead of ventricular fibrillation) and avoids the problem of the operator misinterpreting the failure to shock as a failure of the defibrillator.

Other features of the invention will be apparent from the following description of preferred embodiments, and from the claims.

Figure 1:
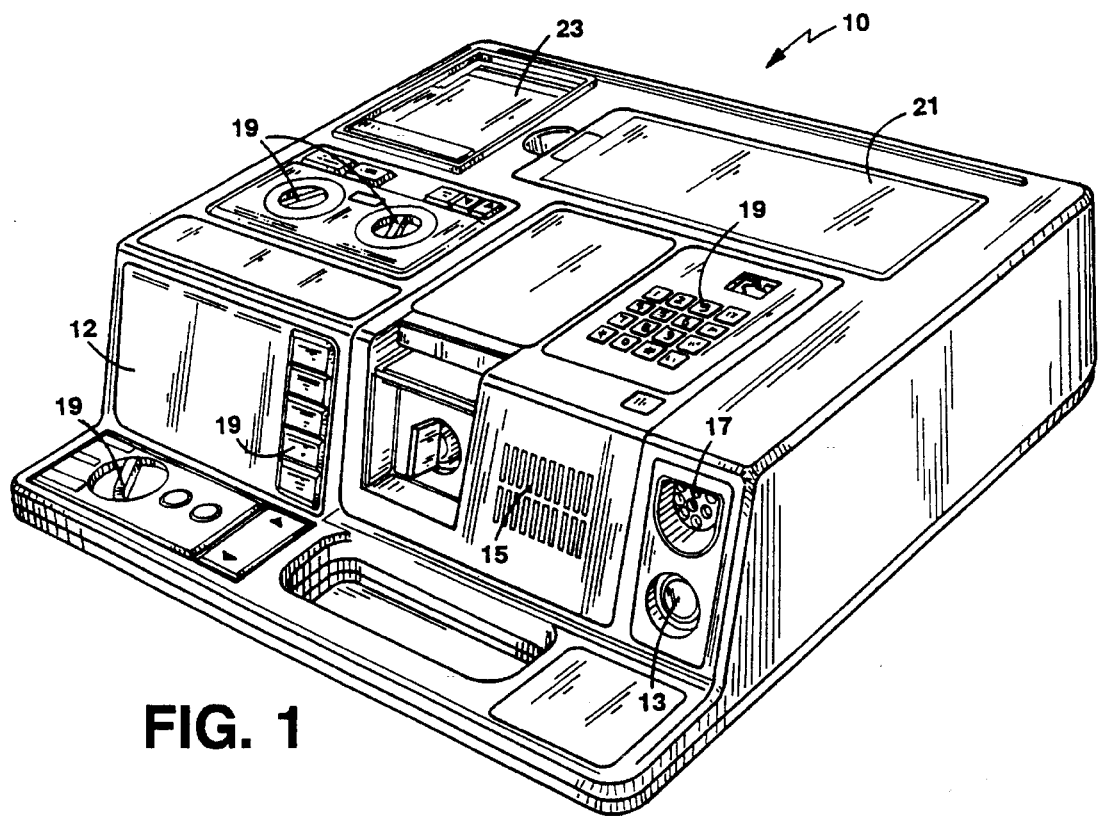
FIG. 1 is a perspective view of a semiautomatic defibrillator embodying the invention.

Shown in FIG. 1 is a semiautomatic defibrillator 10. The defibrillator monitors the electrocardiograph (ECG) signal of a patient (received from ECG electrodes 14), displays the ECG signal (and other information) on a video monitor 12, analyzes the ECG signal to detect shockable waveforms, provides an advisory indication on the monitor (and with voice prompts from speaker 15) when a shockable waveform is detected and a shock is advised, and provides a shock discharge switch 13 by which the user may administer a shock if a shockable waveform has been detected. The shock is delivered through disposable electrodes adhesively applied to the patient's chest. The electrodes are coupled to the defibrillator at connector 17. Optionally, the defibrillator also includes cardiac pacing capability, and both pacing and defibrillation stimuli are delivered through multi-function electrodes 17, which are adhesively adhered to the chest wall. Various control knobs and buttons 19 are provided, some of which are only operable in a manual mode which is only made available to qualified operators. A battery is stored in compartment 21. Strip chart recording can optionally be provided by recorder 23.

Figure 2:
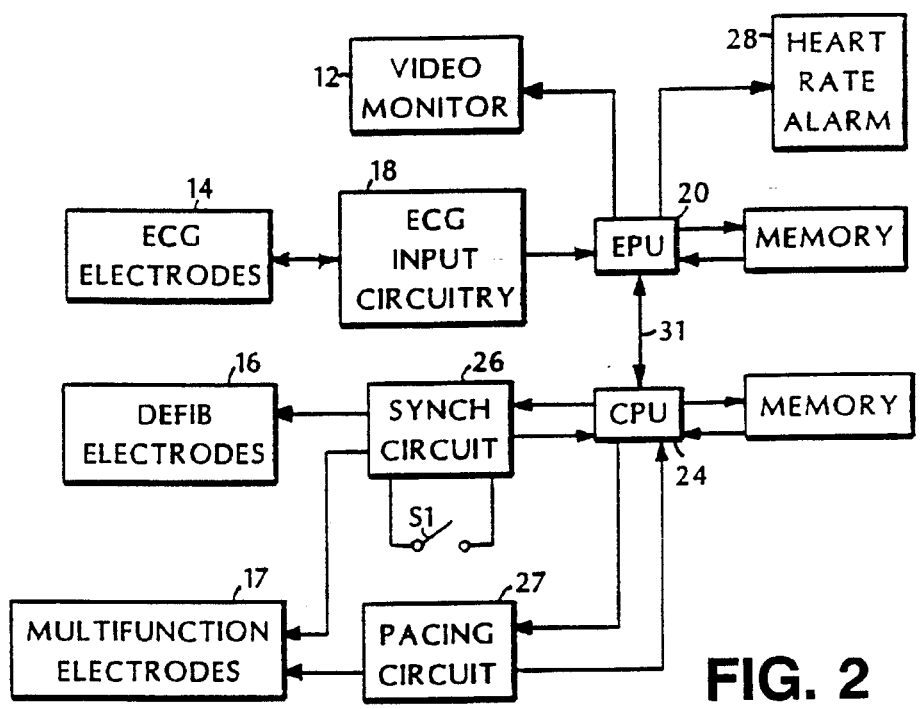
FIG. 2 is a block diagram of the electrical aspects of the defibrillator of FIG. 1.

Turning to the block diagram of FIG. 2, the output of ECG electrodes 14 is received by input circuitry 18 (e.g., input filters and analog-to-digital converters) and fed to ECG processor (EPU) 20. The ECG processor runs the advisory algorithm that processes the ECG signal to detect shockable waveforms, and controls the monitor on which the ECG signal and advisory indications are displayed. The ECG processor communicates with central processor (CPU) 24 via a bidirectional serial interface 31. The ECG processor determines whether a waveform is shockable, and if so at what point in time the shock should be delivered. The shock synchronization point is communicated to the CPU via a hardware interrupt line separate from the normal serial communication interface bus. A hardwired interrupt is used in order to minimize the latency time between the actual cardiac event and the defibrillation shock. A number of factors affect latency time, including delays due to hardwired (analog) filters, software (digital) filters, software waveform analysis algorithms, inter- and intraprocessor communication latencies, interrupt latency, and high-voltage relay actuation time. The latency time should be kept below approximately 60 mS for maximum beneficial effect. The central processor communicates with a shock synchronizing circuit 26, which includes operator-controlled discharge switch S1. A heart rate alarm (both visual and auditory) 28 is also controlled by the ECG processor. If pacing is included in the defibrillator, the central processor also controls a pacing circuit 27, and the pacing stimulus may either be delivered through separate pacing electrodes (not shown) or multi-function electrodes, to which both the defibrillation and pacing outputs are connected.

Figure 5:
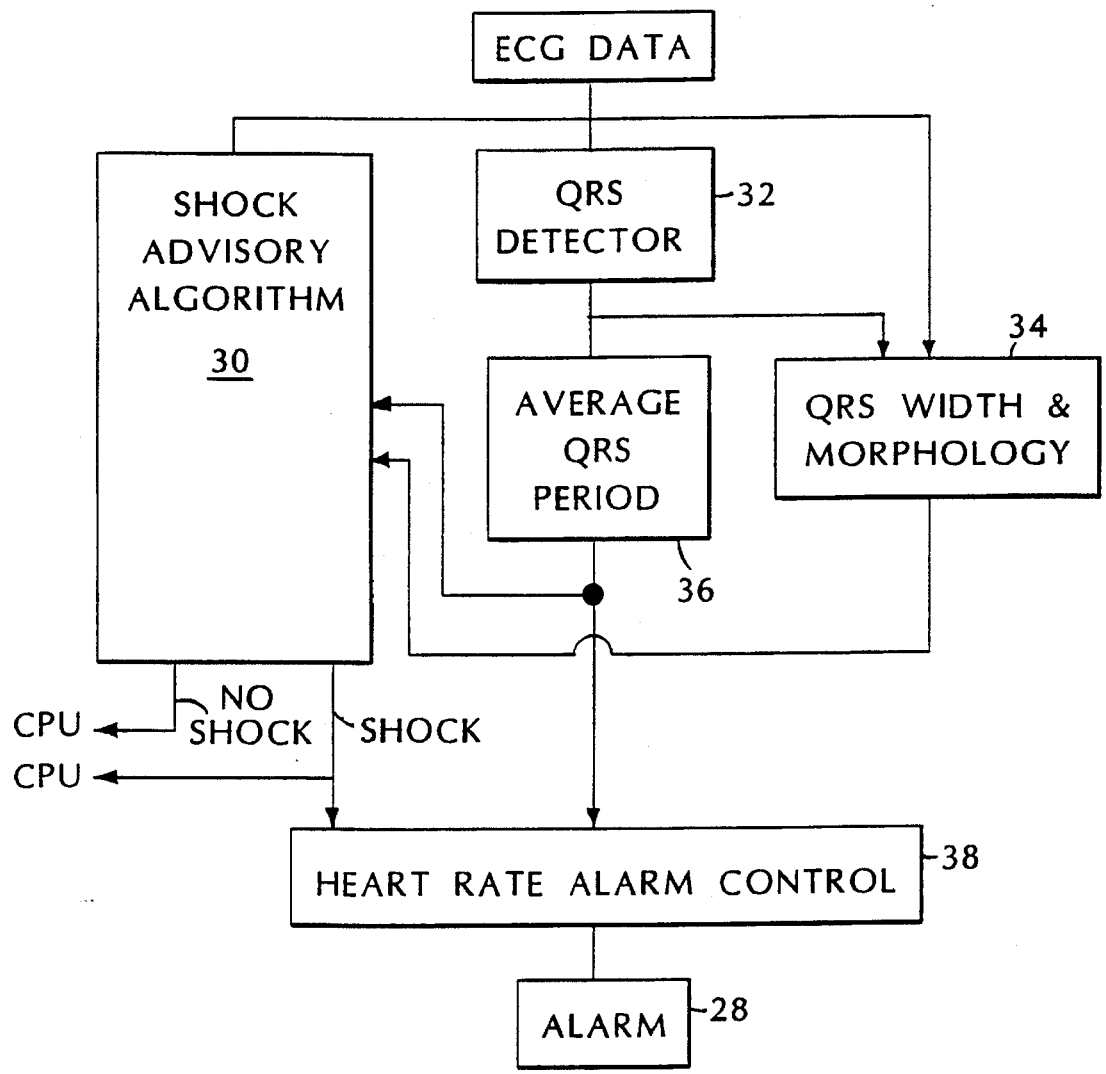
FIG. 5 is a flow chart of the steps followed by the defibrillator of FIG. 1 in activating a heart rate alarm.

The shock advisory algorithm 30 (FIG. 5) implemented by the ECG processor may be of conventional design. The outputs of the algorithm (indicating whether a shock or no-shock decision has been reached) are supplied to the central processor (CPU). The algorithm must be able to distinguish between shockable waveforms (e.g., high-rate tachycardia and ventricular fibrillation) and nonshockable waveforms. And it must also be able to distinguish between high rate tachycardia (VTACH) and ventricular fibrillation (VF), as shock synchronization is performed differently for the two conditions. Algorithms and techniques therefor are taught in U.S. Pat. Nos. 4,919,144; 4,796,620; 4,635,639; 4,619,265; 4,583,553; 4,523,595; 4,453,551; 4,295,474; 4,275,742; 4,202,340; 4,088,138; 3,807,392; 3,805,795; 3,616,790; 3,612,041; and 3,554,187; and in the following publications: W. A. Tacker, Defibrillation of the Heart, 1994 Mosby Yearbook; D. Craig Edwards, "Development of a Decision Algorithm for a Semi-Automatic Defibrillator," Annals of Emergency Medicine, 18:12, Dec. 1989, 1276–1279; C. M. Jack, "An External Automatic Device to Detect Ventricular Fibrillation," European Heart Journal, 7, 1986, 404–411; S. Kuo, "Computer Detection of Ventricular Fibrillation," Computers in Cardiology, Sept. 1978, 347–349; F. K. Forster, "Recognition of Ventricular Fibrillation, Other Rhythms and Noise in Patients Developing the Sudden Cardiac Death Syndrome"; and H. Ozemek, "Detection of Ventricular Fib. by Microcomputer," Journal of Clinical Engineering, Vol. 6, No. 3, 1981, p. 203–207.

The ECG processor also implements a QRS detector 32 (FIG. 5) and a QRS width and morphology detector 34, both as known in the prior art, for example, as taught in U.S. Pat. Nos. 4,667,682; 4,184,487; 4,083,366; 4,034,745; 4,022, 192; 3,978,856; 3,858,574; 3,773,038; 3,650,263; 3,648, 689; 3,513,833; and in the following publications: A. Cohen, Biomedical Signal Processing CRC Press, 1986; W. Thompkins, "A Real Time QRS Detection Algorithm," IEEE Transactions on Biomedical Eng., Vol. BM-C32, No. 3, March 1985, 230–236; C. Mead, "Development and Evaluation of a New QRS Detector/Delineator," Computers in Cardiology, Sept. 1979, 251–254; P. E. Trahanias, "Syntactic Pattern Recognition of the ECG," IEEE Trans. Pattern Anal. Mach. Intell., Vol. PAMI-12, pp. 648–657, July 1990; and M. E. Nygards, "Delineation of the QRS Complex Using the Envelope of the ECG," Med & Biol. Eng. & Computing, Sept. 1983, 538–547.

The average period between QRS wave complexes is calculated (36) by averaging the period of time between R-waves. Average QRS period and QRS width and morphology information are passed to the shock advisory algorithm 30 and to the heart rate alarm control 38, which activates alarm 28.

In addition to supplying the heart rate alarm control with QRS period, the alarm control logic is also supplied with an output of the shock advisory algorithm indicating whether a shockable waveform has been detected. The control logic activates the heart rate alarm when the algorithm has detected a shockable waveform or the average QRS period exceeds a threshold. The alarm is provided visually on monitor 12 and audibly by speaker 15 (e.g., by a "CHECK PATIENT" warning). The alarm logic can also optionally control whether the stimulus delivered is a defibrillation shock or a pacing stimulus; e.g., if asystole or bradycardia (zero or low heart rate) is detected, the stimulus delivered could be a pacing stimulus. For instance, it is not uncommon for the patient suffering from cardiac arrest to be converted with defibrillation to a bradycardiac rhythm which is properly treated with pacing. Thus, after defibrillation, if bradycardia is detected, the patient could be automatically treated with pacing stimuli.

If the output of the shock advisory algorithm advises delivery of a shock, a message to that effect is displayed on monitor 12. The operator may then administer the shock by closing switch S1. But unlike the operation in conventional semiautomatic defibrillators, the shock is not immediately administered when the operator activates switch S1. Instead, the defibrillator delays administration of the shock in an effort to synchronize its delivery with a desired ECG event. If the advisory algorithm has detected high-rate tachycardia, then the triggering ECG event is the occurrence of an R-wave. On the other hand, if the advisory algorithm has detected ventricular fibrillation, the triggering ECG event is a high peak in the ECG (e.g., an absolute ECG signal level greater than a predetermined percentage of the average absolute magnitude of the ECG).

Figure 3:
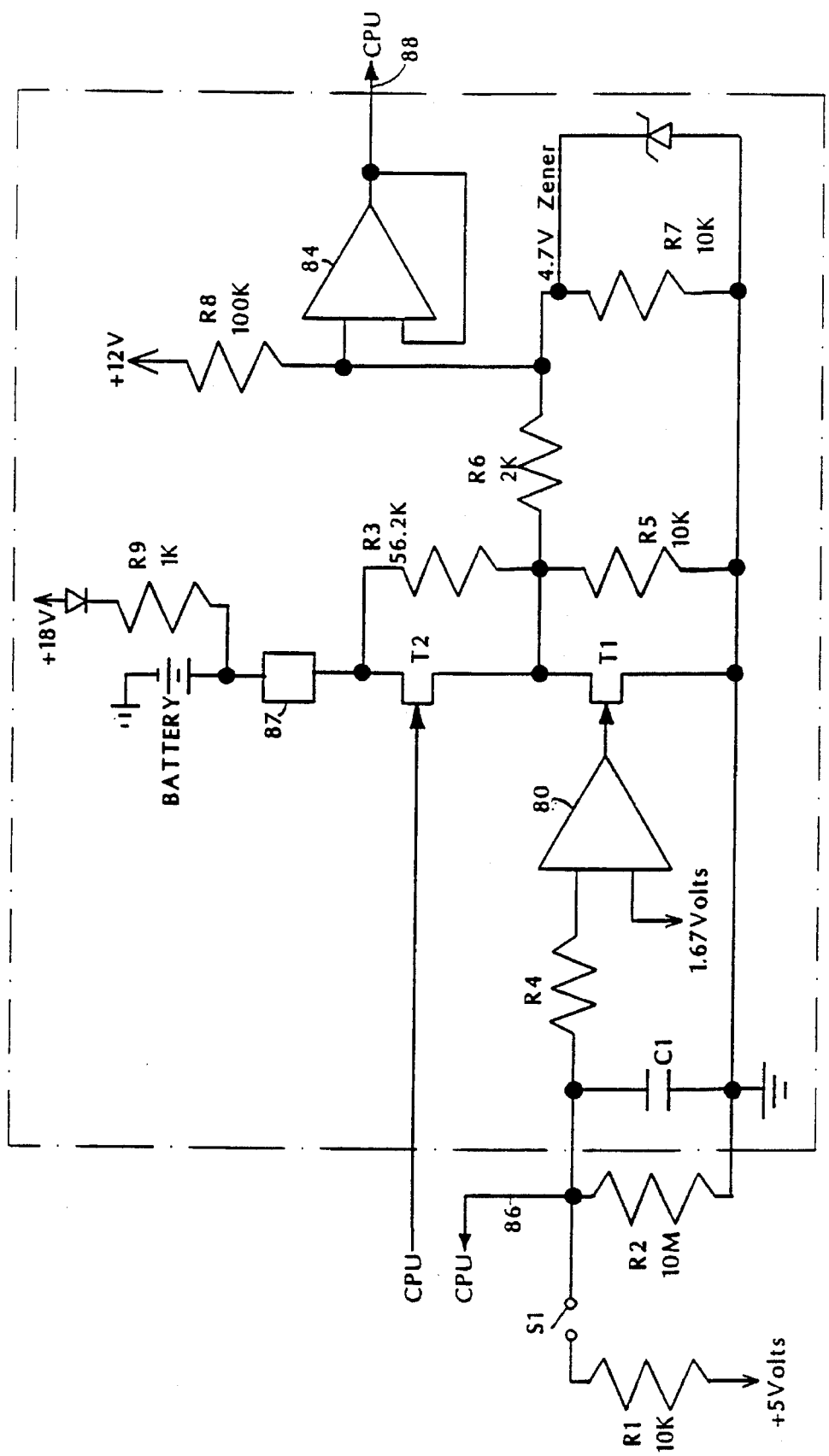
FIG. 3 is a circuit diagram of the shock timing circuit of FIG. 2.
Figure 4:
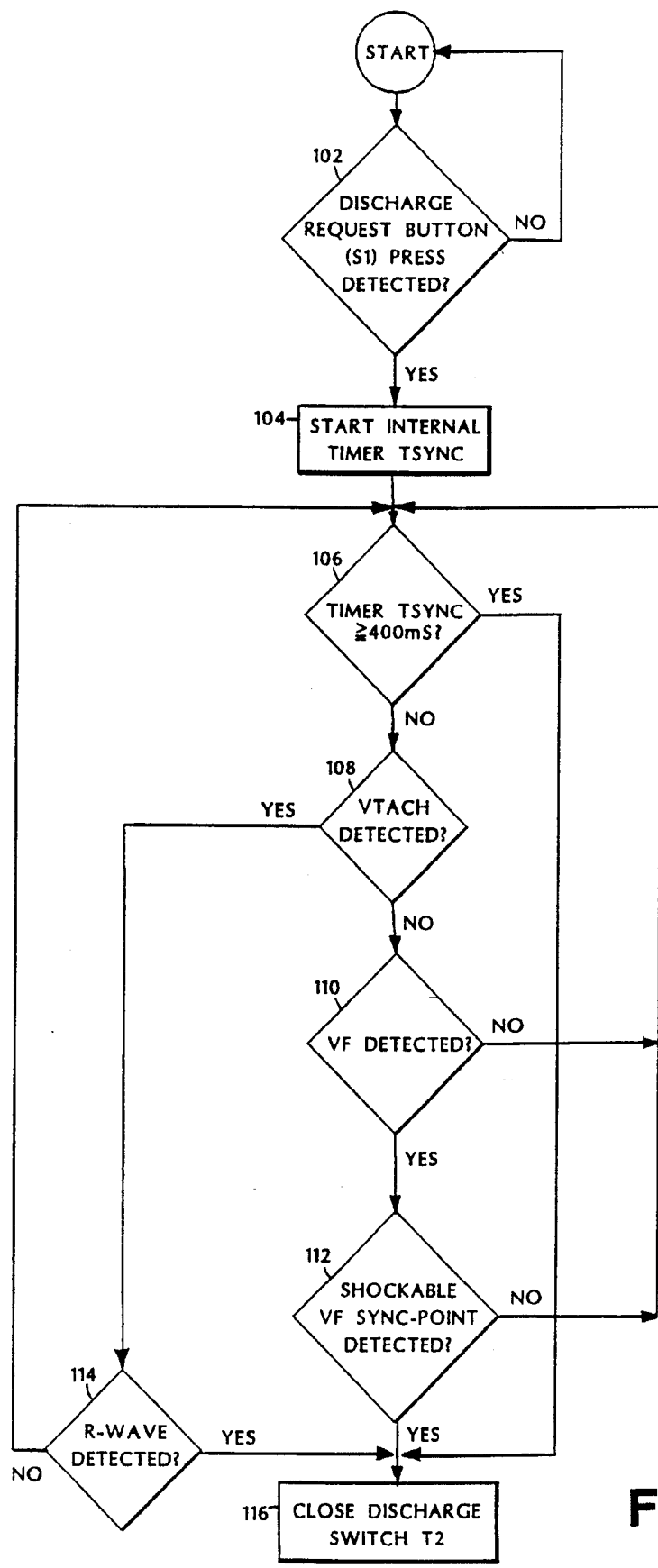
FIG. 4 is a flow chart of the steps followed by the defibrillator of FIG. 1 in delivering a shock.

Synchronization is accomplished using the synchronizing circuit of FIG. 3 and the processor-implemented steps of FIG. 4. When the processor detects (102, FIG. 4) that the user has closed discharge request switch S1 (FIG. 3), a software-implemented 400 msec timer TSYNCH is started (104). Closure of switch S1 also has the effect of closing FET switch T1 for a period of about 500 msec (the period set by the delay circuit comprised of C1, R2 and the comparator 80). During the next 400 msec period, the processor determines whether the advisory algorithm has detected high rate tachycardia (VTACH) (108) or ventricular fibrillation (VF) (110). If high rate tachycardia has been detected by the algorithm, then the processor waits for detection of a R-wave (114). If an R-wave is detected, the processor initiates delivery of a shock to the patient, by activating discharge FET switch T1, which, in turn, activates patient relay coil 82 (FIG. 3). If ventricular fibrillation has been detected, the processor waits for detection of VF synch-point in the ECG signal (e.g., an absolute ECG signal level greater than a predetermined percentage of the average absolute magnitude of the ECG). If the synch-point is detected, the processor delivers a shock to the patient (by activating switch T1). If the 400 msec period expires (106, FIG. 4) without a triggering ECG event being detected, the processor still initiates delivery of a shock.

The processor is able to check the integrity of FET switches T1, T2, and other aspects of the circuit of FIG. 3, by sampling the voltages at two points (86, 88). The circuit provided by resistors R3, R5–R9 and amplifier 84 aid in this diagnosis.

Other embodiments are within the scope of the following claims. For example, the maximum delay period between closure of switch S1 and administration of the shock may be varied (preferably within a range of 50 msec to 5 Sec).

What is claimed is:

1. A semiautomatic cardiac defibrillator for receiving an ECG signal from a patient, providing an advisory indication to an operator, and allowing the operator to initiate delivery of a defibrillating shock to a patient through electrodes adapted for application to the patient's chest, said defibrillator comprising:

an input circuit operable to receive an ECG signal from the patient;

processing circuitry connected to the input circuit and operable to process the received ECG signal to determine whether to issue an advisory indication recommending delivery of a shock, to issue the advisory indication recommending delivery of the shock, and to process the ECG signal to recognize a shock-triggering event;

a display operable to receive the advisory indication from the processing circuitry and to display the advisory indication to the operator;

defibrillation circuitry operable to generate a defibrillating shock and to deliver the defibrillating shock to the electrodes;

a manually operable switch by which an operator, following display of an advisory indication recommending delivery of a shock, initiates delivery of the defibrillating shock to the patient, the switch being configured to be moved by the operator to a deliver-shock position in which the switch generates a request for a shock if there is an advisory indication recommending delivery of a shock; and shock synchronizing circuitry operable to detect the request for a shock from the switch, to activate the defibrillation circuitry in response to the request for a shock to thereby cause the defibrillation circuitry to deliver the defibrillating shock to the electrodes, and to automatically delay activation of the defibrillation circuitry, independently of whether the switch remains in the deliver-shock position, until the shock-triggering event is recognized by the processing circuitry.

2. The semiautomatic defibrillator of claim 1 wherein the shock synchronizing circuitry only activates the defibrillation circuitry if the shock-triggering event is recognized by the processing circuitry within a maximum predetermined period.

3. The semiautomatic defibrillator of claim 1 wherein the shock synchronizing circuitry activates the defibrillation circuitry at the end of a predetermined period whether or not the shock-triggering event is recognized by the processing circuitry.

4. The semiautomatic defibrillator of claim 1 or 3 wherein the processing circuitry is operable to recognize an R-wave as the shock-triggering event when the processing circuitry has issued an advisory indication recommending delivery of a shock in response to detection of high rate tachycardia.

5. The semiautomatic defibrillator of claim 1 or 3 wherein the processing circuitry is operable to recognize a relatively larger absolute signal level in the ECG signal as the shock-triggering event when the processing circuitry has issued an advisory indication recommending delivery of a shock in response to detection of ventricular fibrillation.

6. The semiautomatic defibrillator of claim 1 or 3 wherein the defibrillation circuitry may be activated only by the shock synchronizing circuitry.

7. A method of semiautomatic cardiac defibrillation, in which an ECG signal is received from a patient, an advisory indication is provided to an operator, and the operator is allowed to initiate delivery of a defibrillating shock to a patient through electrodes applied to the patient's chest, the method comprising the steps of:

receiving an ECG signal from the patient;

processing the received ECG signal to determine whether to issue an advisory indication recommending delivery of a shock;

issuing the advisory indication recommending delivery of the shock;

processing the received ECG signal to recognize a shock-triggering event;

displaying the advisory indication to the operator;

permitting delivery of a defibrillating shock to the electrodes when a manually operable switch is moved by the operator to a deliver-shock position indicative of a request by the operator for delivery of the defibrillating shock to the electrodes;

automatically delaying delivery of the defibrillating shock, after delivery of the defibrillating shock to the electrodes has been permitted by movement of the switch, until the shock-triggering ECG event is recognized, independently of whether the switch remains in the deliver-shock position; and delivering the defibrillating shock to the electrodes after the shock-triggering ECG event has been recognized and delivery of the defibrillating shock has been permitted by movement of the switch.

8. The method of claim 7 wherein the step of delivering the defibrillating shock comprises delivering the defibrillating shock only if the shock-triggering ECG event is recognized within a predetermined period.

9. A method of semiautomatic cardiac defibrillation, in which an ECG signal is received from a patient, an advisory indication is provided to an operator, and the operator is allowed to initiate delivery of a defibrillating shock to a patient through electrodes applied to the patient's chest, the method comprising the steps of:

receiving an ECG signal from the patient;

processing the received ECG signal to determine whether to issue an advisory indication recommending delivery of a shock;

issuing the advisory indication recommending delivery of the shock;

processing the received ECG signal to recognize a shock-triggering event;

displaying the advisory indication to the operator;

permitting delivery of a defibrillating shock to the electrodes when a manually operable switch is moved by the operator to a deliver-shock position indicative of a request by the operator for delivery of the defibrillating shock to the electrodes;

automatically delaying delivery of the defibrillating shock, after delivery of the defibrillating shock to the electrodes has been permitted by movement of the switch, until the shock-triggering ECG event is recognized, independently of whether the switch remains in the deliver-shock position; and delivering the defibrillating shock after delivery has been permitted by movement of the switch and either after the shock-triggering ECG event has been recognized or at the end of the predetermined period whether or not the shock-triggering event has been recognized.

10. The method of claim 7 or 9 wherein the step of processing the received ECG signal to recognize a shock-triggering event comprises recognizing an R-wave as the shock-triggering event when the advisory action recommending delivery of the shock is issued in response to detection of high rate tachycardia.

11. The method of claim 7 or 9 wherein the step of processing the received ECG signal comprises recognizing a relatively larger absolute signal level in the ECG signal as the shock-triggering event when the advisory action recommending delivery of the shock is issued in response to detection of ventricular fibrillation.

* * * * *